US006225526B1

(12) United States Patent
Flügge et al.

(10) Patent No.: US 6,225,526 B1
(45) Date of Patent: May 1, 2001

(54) DNA MOLECULES WHICH CODE FOR A PLASTID 2-OXOGLUTARATE/MALATE

(75) Inventors: Ulf-Ingo Flügge; Andreas Weber, both of Köln; Karsten Fischer, Hürth-Efferen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/191,275

(22) Filed: Nov. 12, 1998

Related U.S. Application Data

(62) Division of application No. 08/750,723, filed as application No. PCT/EP95/02319 on Jun. 14, 1995, now Pat. No. 5,981,219.

(30) Foreign Application Priority Data

Jun. 15, 1994 (DE) .................................................. 44 20 782

(51) Int. Cl.[7] .......................... C12N 15/29; C12N 15/82; C12N 5/04; A01H 5/00; A01H 5/10
(52) U.S. Cl. ......................... 800/278; 800/284; 435/419; 435/468; 435/69.1
(58) Field of Search .................................... 800/284, 278; 435/468, 69.1, 419

(56) References Cited

U.S. PATENT DOCUMENTS 5,608,146 * 3/1997 Frommer et al. ..................... 800/205

FOREIGN PATENT DOCUMENTS

| 0 255 340 A1 | 2/1988 | (EP) . |
| WO 93/10251 | 5/1993 | (WO) . |
| WO 94/01559 | 1/1994 | (WO) . |
| WO 94/10320 | 5/1994 | (WO) . |

OTHER PUBLICATIONS

EMBL Sequence Database, Rel. 42, Dec. 13, 1994, Acc. No. U13238, Spinacia Oleracea Polka Chloroplast Envelope Membrane 2–Oxoglutarate/Malate Translocator (SODiT1) MRNA, Complete CDs.

Fischer, K., et al., "Cloning and in vivo Expression of Functional Triose Phosphate/Phosphate Translocators from $C_3$–and $C_4$–Plants:Evidence for the Putative Participation of Specific Amino Acid Residues in the Recognition of Phosphoenolpyruvate," *The Plant Journal*, 5(2), pp. 215–228 (1994).

Genchi, G., et al., Partial Purification and Reconstitution of the α–Ketoglutarate Carrier from Corn (*Zea mays* L.) Mitochondria, *Plant Physiol.*, 96, pp. 1003–1007 (1991).

Menzlaff, E. and U. Flügge, "Purification and Functional Reconstitution of the 2–oxoglutarate/malate Translocator from Spinach Chloroplasts," *Biochim. Biophys. Acta*, 1147, pp. 13–18 (1993).

Riesmeier, J.W., et al., "Antisense Repression of the Chloroplast Triose Phosphate Translocator Affects Carbon Partitioning in Transgenic Potato Plants," *Proc. Natl. Acad. Sci.* 90, pp. 6160–6164 (1993).

Runswick, M.J., et al., "Sequence Of The Bovine 2–Oxoglutarate/Malate Carrier Protein: Structural Relationship To Other Mitochondrial Transport Proteins," *Biochemistry*, 29, pp. 11033–11040 (1990); and.

Weber, A., et al., "The 2–Oxoglutarate/Malate Translocator of Chloroplast Envelope Membranes: Molecular Cloning of a Transporter Containing a 12–Helix Motif and Expression of the Functional Protein in Yeast Cells," *Biochemistry*, 34, pp. 2621–2627 (1995).

* cited by examiner

*Primary Examiner*—David T. Fox
(74) *Attorney, Agent, or Firm*—Fish & Neave; James F. Haley, Jr.; Karen E. Brown

(57) ABSTRACT

DNA molecules are described which code for a plastid 2-oxoglutarate/malate translocator, particularly from *Spinacia oleracea*, as well as bacteria, fungi, transgenic plant cells and transgenic plants containing such DNA molecules.

18 Claims, 4 Drawing Sheets

DNA MOLECULES WHICH CODE FOR A PLASTID 2-OXOGLUTARATE/MALATE

This application is a divisional of application Ser. No. 08/750,723 filed Dec. 12, 1996, now U.S. Pat. No. 5,981,219, which is a 371 of PCT/EP95/02319 filed Jun. 14, 1995.

BACKGROUND OF THE INVENTION

The present invention relates to DNA molecules, particularly from *Spinacia oleracea*, containing the coding region of a 2-oxoglutarate/malate transporter and the introduction of which into a plant genome modifies the production and transport of carbon skeletons for nitrogen fixation and the transport of the assimilated nitrogen in transgenic plants. The invention furthermore relates to plasmids, yeasts and bacteria containing said DNA molecules, as well as to transgenic plants in which modifications of the activity of the 2-oxoglutarate/malate transporter and thus modifications of the nitrogen and carbon metabolism are brought about by introduction of said DNA molecules. The invention furthermore relates to transgenic plants the photo-respiratory capability of which is influenced by the modification of the activity of the 2-oxoglutarate/malate transporter. The invention also relates to the use of the DNA molecules described which code for a 2-oxoglutarate/malate translocator for the identification of related translocators from *Spinacia oleracea* and other plants by low-stringency hybridization or by PCR techniques, as well as the use of the 2-oxoglutarate/malate translocator as target for herbicides.

Only plants, bacteria and yeasts are capable of converting on a large scale inorganic nitrogen (nitrate nitrogen) into organically fixed nitrogen (usually in the form of amino acids) by reductively aminating organic carbon compounds. The remainder of the animated world, particularly useful animals and humans, is dependent on plants as primary suppliers of organic nitrogen compounds. Assimilation of inorganic nitrogen in plants by fixation to organic carbon depends on the availability of nitrogen, carbon skeletons and energy.

The nitrogen supply of the plant can be influenced by fertilizers. The energy for nitrogen assimilation is derived from the light reaction of photosynthesis or in roots or other non-green tissues from dissimilation and under normal field conditions is no limiting factor.

2-oxoglutarate (α-ketoglutarate) according to today's knowledge is the primary acceptor of reduced nitrogen in the glutamine synthase/glutamine 2-oxoglutarate aminotransferase (GOGAT) reaction. In this reaction nitrogen (ammonium nitrogen) reduced by glutamine synthase is first transferred onto glutamate under energy consumption. Glutamine is formed. In a sequential reaction the glutamate oxoglutarate aminotransferase (GOGAT; glutamate synthase) catalyzes the transfer of an amino group of glutamine onto 2-oxoglutarate (transamination) while consuming reduction equivalents. Two glutamate molecules are formed.

The entire reaction sequence of the glutamine synthase/GOGAT reaction is localized in the stroma of the plant plastids. These organelles are surrounded by two lipid bilayer membranes, with the exterior having molecular sieve character and being permeable to compounds up to a size of about 10 kD (Flügge and Benz, 1984, FEBS Lett. 169:85–89). The inner membrane is permeable to some smaller compounds such as water, carbon dioxide, oxygen and nitrite, however, not to larger charged molecules such as 2-oxoglutarate.

The key compound of the glutamine synthase/GOGAT reaction, the 2-oxoglutarate, must be moved from the cytosol of the plant cell by a specific translocator across the inner membrane of the chloroplast envelope into the stroma of the plastid. Transport of 2-oxoglutarate into the plastids takes place in exchange with malate from the plastids via the 2-oxoglutarate/malate translocator. The malate exported in this process into the cytosol is transported back by a second translocator, the dicarboxylate translocator, which is related with the 2-oxoglutarate/malate translocator in its substrate specificity, in exchange with glutamate. As a result, 2-oxoglutarate is imported into the chloroplast and the end product of the glutamine synthase/GOGAT reaction, glutamate, is exported without a net transport of malate which circulates via both translocator systems ("double translocator", Woo et al., 1987, Plant Physiol. 84:624–632; Flügge et al., 1988, Planta 174:534–541). Glutamate is the plant's preferred amino group donor in a series of transamination reactions, for example in the biosynthesis of the amino acids alanine or phenylalanine, etc. Furthermore, glutamate is an important transport form for organically bound nitrogen within the plant. Most nitrogen-containing compounds in the plant such as amino acids, nucleic acids or alkaloids require glutamate as primary amino acid donor for their biosynthesis pathway.

The 2-oxoglutarate required for nitrogen assimilation is essentially synthesized by conversion of citrate in the cytoplasm of the cells.

More recent publications (Riesmeier et al., 1993, Proc. Natl. Acad. Sci. USA 90:6160–6164; Heineke et al., 1994, Planta 193:174–180) show that the effectivity of the photosynthetic carbon reaction is inter alia substantially limited by the export of the reduced, organically bound carbon (triose phosphate) formed which is catalyzed by a translocator localized in the inner membrane of the chloroplast envelope. This translocator protein thus is a "bottle-neck" in the carbon metabolism. The plastid 2-oxoglutarate/malate translocator plays a similar role in the nitrogen metabolism.

The plastid 2-oxoglutarate/malate translocator thus plays a key role in the nitrogen metabolism of plants since it is responsible for supplying sufficient amounts of the substrate for nitrogen assimilation by the glutamine synthase/GOGAT reaction. By manipulating the activity of this translocator it would therefore presumably be possible to influence the effectivity of nitrogen assimilation in plants.

Since the majority of humans on earth has to depend on a vegetarian diet, resulting in a continuous inadequate provision with proteins in these social strata, there is an urgent demand for plants having an increased content in organic nitrogen compounds, particularly proteins and amino acids. In the industrialized countries animal and fish meal is increasingly being added to animal feeding stuff to improve the provision of breeding animals with proteins. Forage plants having a higher protein content would surely be the better alternative in particular considering the problems, such as BSE, arising from the feeding of animal meals.

It would be possible to influence the activity of the plastid 2-oxoglutarate/malate translocator via genetic engineering techniques if DNA sequences coding for such a translator were available. So far, this has not been the case. The provision of DNA sequences coding for a 2-oxoglutarate/malate translocator would furthermore allow identification of substances which specifically inhibit said translocator and which can hence be used as herbicides.

Presently, sequences of translocator proteins of the substrate specificity described above are known only from the mitochondria of bovine hearts and from human mitochondria (Runswick et al., 1990, Biochemistry 29:11033–11040;Iacobazzi et al., 1992, DNA Seq. 3(2):79–88). These transporters play an essential role in the mitochondrial dicarboxylate metabolism (inter alia malate/aspartate shuttle, oxoglutarate/isocitrate shuttle) and pertain to the family of mitochondrial metabolite transporters which are closely interrelated. For example, the mitochondrial carriers (phosphate/OH$^-$, ADP/ATP, oxoglutarate/malate, etc.) are characterized by sequence relationship and by the presence of internal repeats. Furthermore, it could be shown for the most mitochondrial carriers as for the 2-oxoglutarate carrier that they are incorporated into the mitochondrial membrane without a presequence (targeting sequence) directing them to the organelles (Runswick et al., 1990, Biochemistry 29:11033–11040). It can thus be presumed that the targeting information is contained in the mature carrier protein. An over-expression of a mitochondrial dicarboxylate transporter in plants would thus not result in an increase in the oxoglutarate transport across the plastid envelope membrane but only in an increase in the mitochondrial dicarboxylate transport, which is an undesired effect.

In contrast to the above, the proteins of the inner envelope membrane of the plastid require a presequence specifically directing them to the plastids (overview articles: Keegstra et al., 1989, Annu. Rev. Plant. Physiol. Plant Mol. Biol. 40:471–501; Lubben et al., 1988, Photosynth. Res. 17:173–194;Flügge , 1990, J. Cell Sci. 96:351–354). In addition to the presequence needed for "plastid targeting", there is further information in the mature part (the part of the protein remaining after cleavage of the presequence by a specific protease) of the plastid envelope membrane proteins which prevents transport of the envelope membrane proteins across the envelope membrane into the plastid stroma or the thylakoid membrane (own, unpublished observations; Li et al., 1992, J. Biol. Chem. 267:18999–19004). So far it has not been possible to exactly localize this information in the mature part of the proteins of the inner envelope membrane known so far (37 kD protein: Dreses-Werringloer et al., 1991, Eur. J. Biochem. 195:361–368; triose-phosphate/phosphate translocator: Flügge et al., 1989, EMBO J. 8:39–46; Willey et al., 1991, Planta 183:451–461; Fischer et al., 1994, Plant Jour. 5(2):215–226; Ca$^{2+}$ ATPase: Huang et al., 1993, Proc. Natl. Acad. Sci. USA 90:10066–10070). Our own investigations conducted with a mitochondrial carrier, the ADP/ATP transporter, showed that this protein cannot or only very ineffectively be directed to the chloroplasts and there be incorporated in the envelope membrane. Even a hybrid protein, consisting of a chloroplastid presequence (containing the information for chloroplast targeting) and said mitochondrial carrier showed only a slight increase in incorporation into the chloroplast envelope membrane as compared to the authentic protein (unpublished observations). Since the protein/lipid interaction is important for a correct insertion and the chloroplastid envelope membrane fundamentally differs in its lipid composition from that of the mitochondria (Joyard et al., 1991, Eur. J. Biochem. 199:489–509), it is highly improbable that an insertion of a mitochondrial protein, albeit a minor one, will be functional, i.e., that a transporter from other organelles can be incorporated at all into the chloroplast envelope membrane in a conformation and orientation corresponding to its function.

Thus, according to the present state of the art, it is not possible to functionally integrate, e.g., mitochondrial or procaryotic dicarboxylate transporters into the inner envelope membrane of the chloroplasts by using known plastid targeting sequences. With the present state of the art it is more promising to achieve the DNA sequence required for the construction of the plants described above by cloning the authentic plastid 2-oxoglutarate/malate translocator.

This cloning, however, cannot be performed by low-stringency screening of a plant cDNA library with a probe derived from the mitrochondrial dicarboxylate transporters. According to what is known today, the chloroplastid translocators have a primary sequence that is completely different from all translocators from other systems (bacteria, mitochondria)—even if the protein has a comparable function. Therefore, the route of biochemical characterization, purification and isolation of the 2-oxoglutarate/malate translocator had to be taken, which is extremely difficult in membrane proteins. Identification of the translocator protein as component of the inner envelope membrane of the chloroplast having an apparent molecular weight of 45,000 Dalton was now possible (Menzlaff and Flügge, 1993, Biochim. Biophys. Acta 1147:13–18). However, the purification procedure described is not suitable to produce sufficient amounts of protein for protein sequencing, since it turned out that the N terminus of the protein was blocked and thus was not available for N-terminal protein sequencing by automated Edman degradation. Therefore, it has not been possible so far to isolate, starting from the amino acid sequence, DNA molecules coding for a plastid 2-oxoglutarate/malate translocator.

The problem underlying the present invention therefore is to provide processes and DNA molecules the use of which makes it possible to modify plants such that they are capable of synthesizing an increased amount of organic nitrogen compounds. Specifically, the problem underlying the invention is to provide DNA molecules coding for a plastid 2-oxoglutarate/malate translocator.

The problem is solved by the provision of the embodiments characterized in the patent claims.

SUMMARY OF THE INVENTION

The present invention therefore relates to DNA molecules coding for a plastid 2-oxoglutarate/malate translocator, with the information contained in the nucleotide sequence leading to the formation of a ribonucleic acid upon introduction and expression in plant cells and allowing introduction of a 2-oxoglutarate/malate translocator activity into the cells via this ribonucleic acid or suppressing an endogenous 2-oxoglutarate/malate translocator activity.

The present invention particularly relates to DNA molecules coding for a protein having the amino acid sequence indicated in Seq ID No:2, as well as DNA molecules comprising the coding region indicated in Seq ID No. 1. It furthermore relates to DNA molecules that hybridize to the aforementioned DNA molecules of the invention, and to DNA molecules the sequence of which is degenerate as a result of the genetic code, with these latter molecules coding for a protein having 2-oxoglutarate/malate translocator activity. Another subject matter of the invention are DNA molecules which are complementary to those mentioned above, as well as fragments and derivatives of the aforementioned DNA molecules according to the invention, which can be derived by, e.g., insertion, substitution or deletion, and code for a 2-oxoglutarate/malate translocator.

The term "hybridization" in the present context is understood to mean hybridization under conventional conditions such as described in, e.g., Sambrook et al. (1989, Molecular Cloning, A Laboratory Manual, 2nd ed., Cold Spring Harbor Laboratory Press, Cold Spring Harbor, N.Y.), preferably hybridization under stringent conditions (likewise described in Sambrook et al., supra).

The DNA molecules (or derivatives or parts of these molecules) of the present invention can be introduced into plasmids that allow a mutagenesis or a sequence modification by recombination of DNA sequences in procaryotic or eucaryotic systems, thereby allowing modification of the specificity of the 2-oxoglutarate/malate translocator. By modifying the specificity of the translocator in direction of improved specificity for glutamate and simultaneous reduced specificity for malate, the "double translocator" system described above could be modified so as to achieve further improved transport rates for 2-oxoglutarate in direct exchange for glutamate. Also, an insensitivity to herbicides specific of the 2-oxoglutarate/malate translocator could be achieved. Standard techniques (Sambrook et al., 1989, Molecular Cloning: A Laboratory Manual, 2nd ed., Cold Spring Harbor Laboratory Press, N.Y., USA) can be employed to bring about base exchanges and/or base deletions and/or to add synthetic or natural sequences. For an interlinkage of the DNA fragments, adapters or linkers can be used. Furthermore, manipulations providing suitable restriction sites or deleting DNA not required can be used. Where insertions, deletions or substitutions such as transitions or transversions are feasible, in vitro mutagenesis, primer repair, restriction or ligation can be used. Methods lending themselves for analysis are generally sequence analysis, restriction analysis and other biochemical molecular biological methods such as the expression of the modified protein in fission yeast and measuring the modified transport properties in artificial liposomes (see Example 4 and Loddenkötter et al., 1993,Proc. Natl. Acad. Sci. USA 90:2155–2159; as well as Fischer et al., 1994, Plant Journal 5:215–226) or measuring the modified transport properties in the protein expressed in transgenic plants using a method which was only recently devised for this purpose by the inventors (Flügge and Weber, 1994, Planta, 194:181–185).

The DNA molecules according to the invention (or parts or derivatives of these molecules) can be used to isolate from the genome of plants similar DNA molecules by standard techniques which likewise code for a 2-oxoglutarate/malate translocator or a similar dicarboxylate translocator. Particularly useful methods are low-stringency hybridization screening of cDNA libraries using the DNA molecule according to the invention or parts thereof as probes or constructions of such probes for stringency and low-stringency screening strategies by deriving degenerate and/or non-degenerate primers from the sequences of the DNA molecules according to the invention for PCR experiments with DNA or cDNA of spinach or other plants. The DNA molecules can also be used to identify and isolate DNA molecules which code for the closely related glutamate-malate translocator (dicarboxylate translocator) of the plastid envelope membrane (subtractive screening methods of a cDNA library from spinach or other plants under varying stringency conditions and with various regions of the DNA molecules according to the invention as probe).

In another embodiment, the present invention relates to the use of the DNA molecules according to the invention or parts or derivatives thereof, derived from these DNA molecules by insertion, deletion or substitution, for the transformation of pro- and eucaryotic cells. In order to guarantee expression of the 2-oxoglutarate/malate translocator in transformed cells, the DNA molecules according to the invention can be introduced into vectors, preferably plasmids, and can be combined with control elements for the expression in procaryotic or eucaryotic cells (see Examples 3 and 5). Such control elements are transcription promoters or transcription terminators. The vectors can be used to transform eucaryotic cells with the purpose of expressing a translatable messenger ribonucleic acid (mRNA) which allows synthesis of a plastid 2-oxoglutarate/malate translocator in the transformed cells or with the purpose of expressing a non-translatable, inversely oriented (anti-sense) messenger ribonucleic acid which prevents synthesis of the endogenous 2-oxoglutarate/malate translocators. For this purpose, also shorter fragments of the DNA molecules according to the invention can be used or DNA molecules the sequence of which has a relatively high degree of homology (more than about 65% homology) to the sequences of the DNA molecules according to the invention. Likewise, expression of endogenous dicarboxylate translocators can be inhibited by the expression of a ribozyme constructed for this purpose and using the DNA molecules according to the invention.

In another embodiment, the present invention therefore relates to recombinant DNA molecules, for example plasmids, comprising one of the DNA molecules according to the invention, e.g., plasmids pBinAR-211 (DSM 9239), pEVP11-211 (DSM 9237) and pBSC-211 (DSM 9238).

The subject matter of the invention are particularly recombinant DNA molecules in which a DNA molecule according to the invention is linked with DNA sequences which allow expression in pro- or eucaryotic cells.

In another embodiment, the present invention relates to bacteria containing DNA molecules according to the invention or recombinant DNA molecules according to the invention.

The present invention furthermore relates to proteins having the activity of a 2-oxoglutarate/malate translocator which are coded for by the DNA sequence of one of the DNA molecules according to the invention. Preferred proteins are those from dicotyledonous or monocotyledonous plants, particularly from plants of the family of Chenopodiaceae and particularly preferred from *Spinacia oleracea*.

The production of such proteins can be achieved in that, e.g., DNA molecules according to the invention which code for a 2-oxoglutarate/malate translocator are linked with DNA sequences which ensure transcription in pro- or eucaryotic cells. The resulting recombinant molecules can then be introduced into and expressed in suitable pro- or eucaryotic host cells. The resulting protein can be isolated according to known methods. It is also possible to express a shortened protein which contains no signal sequences allowing localization of the protein in the inner envelope membrane of the plastids.

In another preferred embodiment, the present invention relates to the use of the DNA molecule according to the invention for the expression of a 2-oxoglutarate/malate translocator in plant cells.

By expressing a RNA corresponding to the DNA molecules according to the invention coding for a plant 2-oxoglutarate/malate translocator it is possible to modify the plant nitrogen metabolism. The economic importance thereof is that an improvement of the transport of 2-oxoglutarate from the cytosol into the plastid results in a modification of the ratio of carbohydrates (sugar, starch, organic acids) and fats in favor of the nitrogen compounds (amino acids, proteins, possibly alkaloids). In this manner, plants can be generated that are richer in valuable protein but exhibit a reduced content of carbohydrates and fats. This modification increases the nutritional value of plants and thus also their economic value.

Methods for the genetic modification of dicotyledonous and monocotyledonous plants are already known (Gasser and Fraley, 1989, Science 244:1293–1299; Potrykus, 1991, Ann. Rev. Plant Mol. Biol. Plant Physiol. 42:205–225). For an expression of coding sequences in plant these have to be linked with transcriptional regulatory elements. Such elements, referred to as promoters, are known (inter alia Köster-Töpfer et al., 1989, Mol. Gen. Genet. 219:390–396). Furthermore, the coding regions have to be provided with the transcription termination signal for them to be correctly transcribed. Such elements were also already described (Gielen et al., 1989, EMBO J. 8, 23–29). The transcriptional start region can be both native or homologous and foreign or heterologous to the host plant. Termination regions are freely interchangeable. The DNA sequence of the transcription start and termination regions can be synthetically produced or obtained from natural sources or can contain a mixture of synthetic and natural DNA components.

For the preparation of the introduction of foreign genes into higher plants there is a large number of cloning vectors available which contain a replication signal for *E. coli* and a marker allowing selection of the transformed cells. Examples of vectors are pBR322, pUC series, M13mp series, pACYC 184 etc. Further DNA sequences may be necessary depending on the method of introduction of desired genes into plants. If, e.g., the Ti or Ri plasmid is used to transform the plant, at least the right border, often, however, the right and the left border of the Ti and Ri plasmid T-DNA must be added to the genes to be introduced as flanking region. The use of T-DNA for the transformation of plant cells has been thoroughly examined and sufficiently described (Hoekema in: The Binary Plant Vector System, Offsetdrukkerij Kanters B-V. Ablasserdam, 1985, Chapter V; Fraley et al., Critic. Rev. Plant Sci. 4:1–46; An et al., 1985, EMBO J. 4:277–287). Once the introduced DNA is integrated into the genome it usually is stable there and is preserved in the progeny of the originally transformed cells. Normally, it contains a selection marker which imparts to the transformed plant cells a resistance to biocides or antibiotics such as kanamycin, bleomycin or hygromycin. The individually introduced maker will therefore allow selection of transformed cells vis-à-vis cells lacking the introduced DNA.

There are many techniques other than the transformation with agrobacteria to introduce DNA in a plant host cell. These techniques include the transformation of protoplasts, microinjection of DNA, electroporation as well as ballistic methods. Whole plants can then be regenerated from the transformed plant material in a suitable selection medium. The plants obtained in this manner can be tested by conventional methods of molecular biology for the presence of the introduced DNA. These plants can be normally grown and cross-bred with plants possessing the same transformed hereditary information or a different hereditary information. The resulting hybrid individuals have the corresponding phenotypic properties.

Therefore, the present invention also relates to transgenic plant cells containing the recombinant DNA molecules according to the invention, as well as transgenic plants reproducible from these transgenic plant cells and transgenic plants containing plant cells according to the invention. These plant cells and plants are characterized in that they contain a recombinant DNA molecule integrated into the genome-which allows expression of a protein having the activity of a 2-oxoglutarate/malate translocator or the expression of a non-translatable RNA molecule inhibiting the synthesis of 2-oxoglutarate/malate translocators. Furthermore, the present invention relates to seed of the transgenic plants according to the invention.

In another embodiment, the present invention relates to the heterologous expression of the DNA molecules according to the invention in fungi, e.g., in fission yeasts (Examples 3, 4 and Loddenkötter et al., 1993, Proc. Natl. Acad. Sci. USA 90:2155–2159), particularly for structural-functional studies of the 2-oxoglutarate/malate translocator, which may lead to the development of a specific inhibitor for this protein. In this context also the development of herbicides is conceivable, since the inhibition of a protein having a key role in the metabolism would inevitably be lethal for the plant.

Therefore, the DNA molecules according to the invention (or parts of these molecules or derivatives of these molecules) can thus be introduced into vectors and can be provided with control elements for the expression in fungal cells, particularly in fission yeasts (see Example 3). The introduction of the 2-oxoglutarate/malate translocator results in a substantial increase in the activity of the 2-oxoglutarate/malate translocator in the recombinant yeast cells which activity can be measured by reconstitution in artificial liposomes. It should be noted in this context that mitochondria possess a 2-oxoglutarate/malate translocator which is similar in its substrate specificity to that of the plastids, which, however, is not similar to the plastid translocator as regards its DNA and amino acid sequence (Runswick et al., 1990, Biochemistry 29:11033–11040). In recombinant yeast cells an up to 100-fold higher malate transport activity is detectable. It is therefore conceivable to modify yeast cells such that they exhibit a modified protein content by using the DNA molecules according to the invention (or parts or derivatives of these molecules). For this purpose, the advantage of the plastid translocator from plants, namely that it is not subject to the endogenous regulatory and compartment targeting mechanisms of fission yeasts, would come in useful. It is highly probable that the described increase in malate transport activity in the yeast cells would not be possible by an expression of a mitochondrial 2-oxoglutarate translocator. These strains would be of utmost importance for the feeding stuff industry.

Thus, the invention also relates to fungal cells, particularly to yeast cells, containing a DNA molecule according to the invention or a recombinant DNA molecule.

The DNA molecules according to the invention contain regions in the coding region which are capable of specifically directing the protein synthesized in the cytoplasm on the ribosomes to plastids and to prevent occurrence of the protein in other membrane systems of the cell. The protein region which directs the protein coded for by the DNA molecules according to the invention to the plastids is located within the first hundred amino acids of the protein, is not required for the transport function of the protein and is removed after successful insertion of the protein in the chloroplast envelope membrane. By exchanging this plastid targeting sequence with one of the known targeting sequences for, e.g., mitochondria, the translocator protein could be directed to another membrane system of eucaryotic cells and could there possibly modify the transport properties across the respective membrane. Likewise, the plastid targeting sequence of the 2-oxoglutarate/malate translocator, particularly the first 100 amino acids, or endogenous regions of the mature protein could be used to direct foreign proteins (e.g., proteins catalyzing the active or passive transport of metabolites across membranes, enzymes, bacterial transport proteins or transporters from yeasts) to the plastids, particularly the plastid envelope membrane, to the plastid stroma or to the thylakoids of plant cells.

On Jun.9, 1994 the following plasmids were deposited in the *E. coli* strains indicated with the recognized international depository Deutsche Sammlung von Mikroorganismen (DSM) [German collection of microorganisms] in Brunswick, Federal Republic of Germany, in accordance with the stipulations of the Budapest Treaty:

| Plasmid | pBinAR-211 | (DSM 9239) |
| Plasmid | pEVP11-211 | (DSM 9237) |
| Plasmid | pBSC-211 | (DSM 9238) |

The Figure shows the uptake of [$^{14}$C] malate in reconstituted liposomes containing *S. pombe* cell membranes.

Figure 2A:
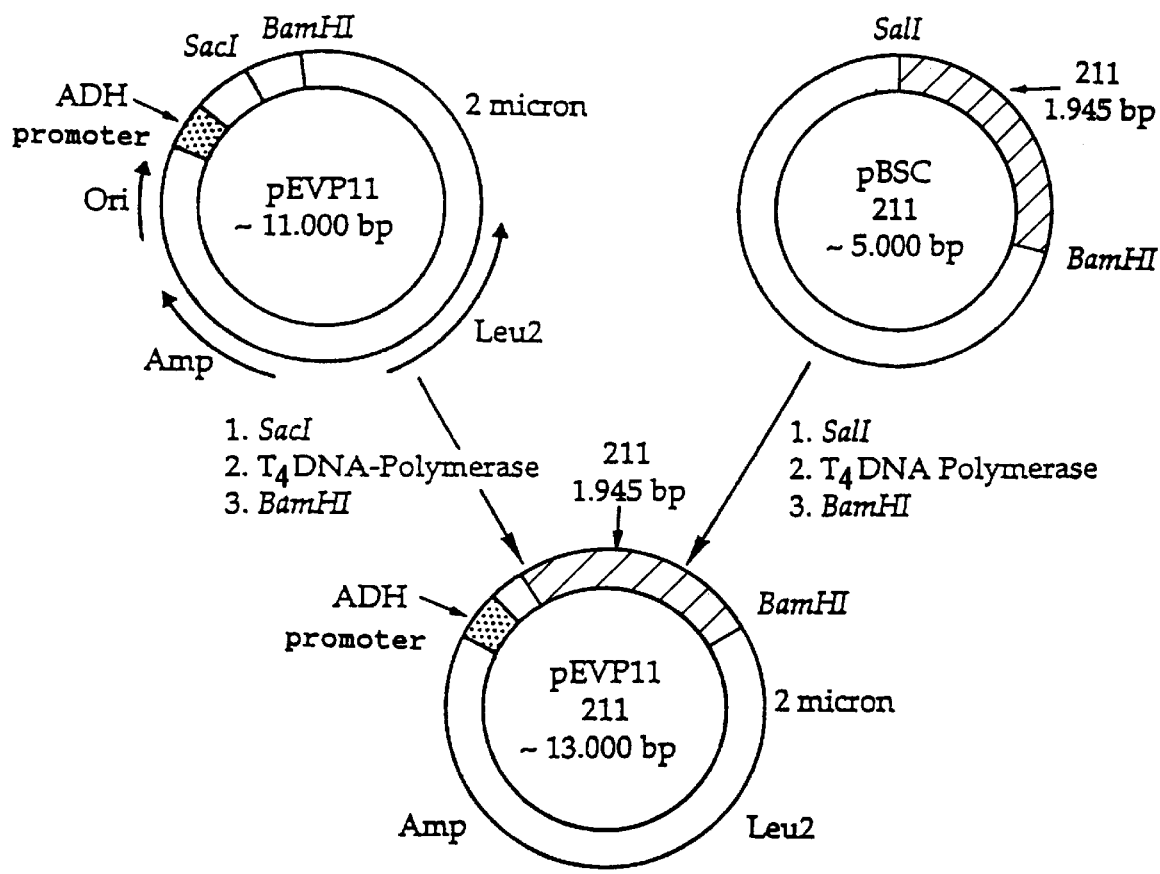
Figure 2B:
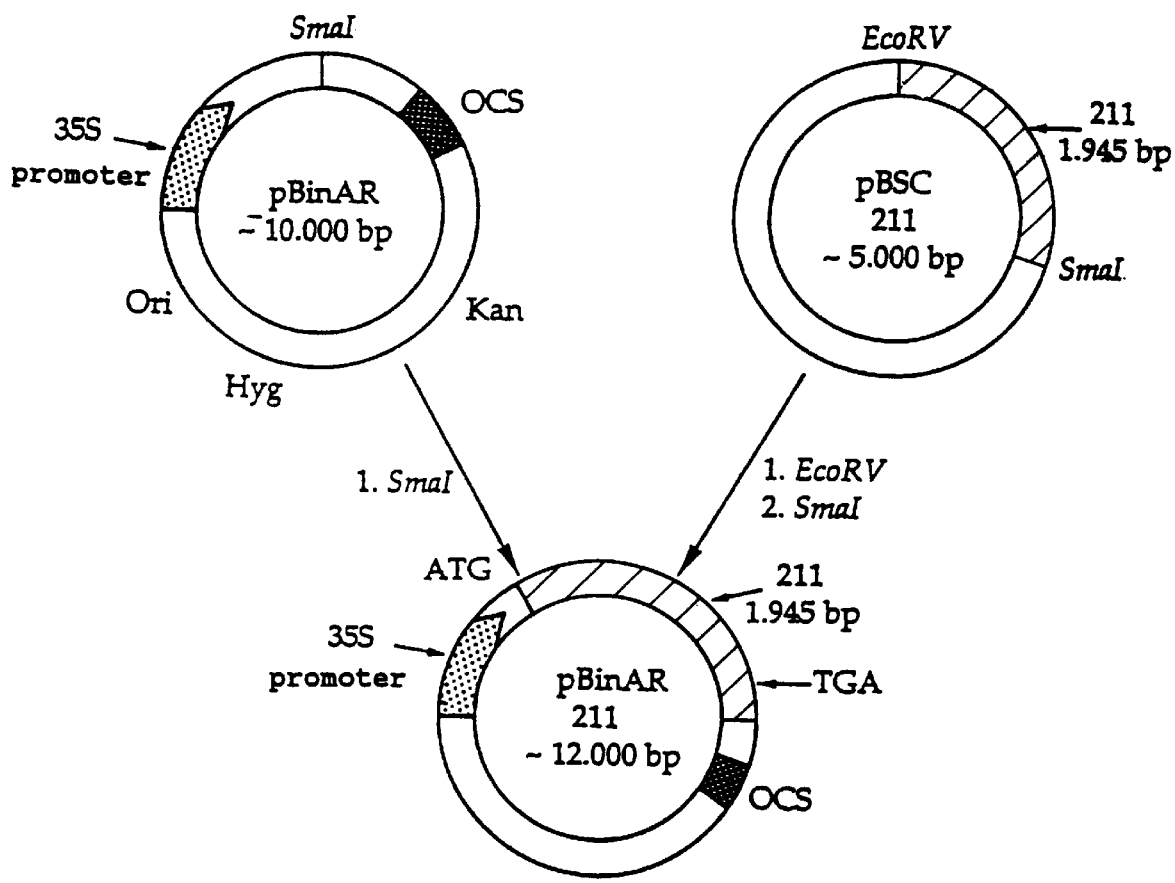

FIGS. 2A–2B: Schematic view of the cloning of plasmid 11-211 (FIG. 2A) and of plasmid pBinAR-211 (FIG. 2B)

Figure 3:
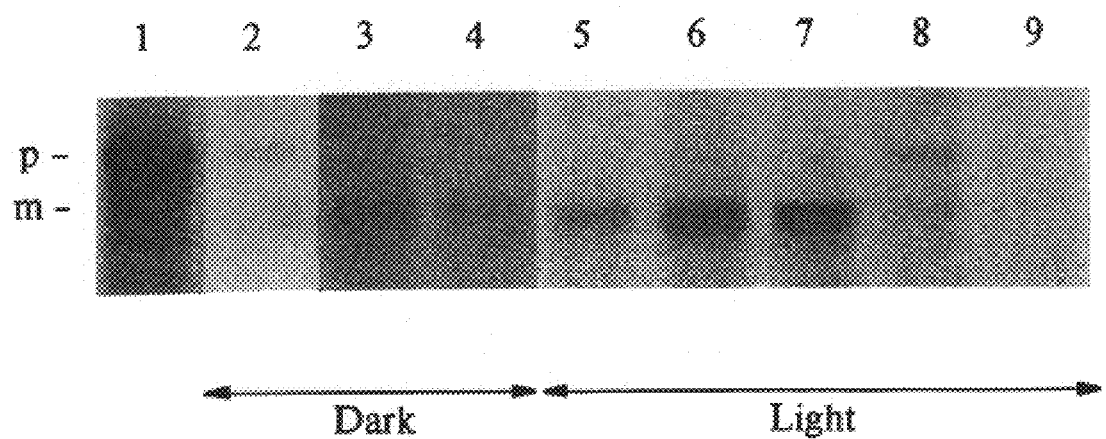

FIG. 3: Targeting of the 2-oxoglutarate/malate translocator precursor protein to the chloroplasts and energy-dependent insertion of the mature protein in the inner envelope membrane SDS polyacrylamide gel electrophoresis was carried out as described in Example 6:
Lane 1: in vitro translated precursor protein
Lanes 2–4: dark conditions
Lanes 5–9: light conditions
Lane 2: without ATP
Lane 3: plus 2 mM ATP
Lane 4: plus 2 mM ATP, subsequent treatment with protease (100 µg/ml)
Lane 5: without ATP
Lane 6: plus 2 mM ATP
Lane 7: plus 2 mM ATP, subsequent treatment with protease (100 µg/ml)
Lane 8: plus decoupling agent (10 µM CCCP)
Lane 9: plus 2 mM ATP; protease-pretreated chloro-plasts (30 µg/ml)

DETAILED DESCRIPTION OF THE INVENTION

For a better understanding of the examples underlying the present invention, some of the methods used are explained in more detail in the following.

1. Cloning Methods

For cloning phage lambda gt10 as well as the vector pBluescript II KS (pBSC) (Short et al., 1988, Nucl. Acids Res. 16:7583–7600) were used.

For the transformation of yeasts vector pEVP11 (Russel and Nurse, 1986, Cell 45:145–153) was used.

For plant transformation the gene constructs were cloned into the binary vector pBinAR (Höfgen and Willmitzer, 1990, Plant Sci. 66:221–230).

2. Bacteria and Yeast Strains

For the pBluescriptKS (pBSC) vector as well as for the pEVP11 and-pBinAR constructs *E. coli* strains DH5α (Hanahan et al., 1983, J. Mol. Biol. 166:557–580) and TG1 (Gibson, 1984, Ph.D. Thesis, Cambridge University, England) were used.

Transformation of the pBinAR constructs in tobacco plants was carried out with the *Agrobacterium tumefaciens* strain LBA4404 (Bevan, 1984, Nucl. Acids Res. 12:8711:8720).

3. Transformation of *Agrobacterium Tumefaciens*

The transfer of the DNA into the Agrobacteria was brought about by the direct transformation according to the method by Höfgen and Willmitzer (1988, Nucl. Acids Res. 16:9877). The plasmid DNA of transformed Agrobacteria was isolated according to the method by Birnboim and Doly (1979, Nucl. Acids Res. 7:1513–1523) and analyzed by gel electrophoresis for correctness and orientation after suitable restriction digestion.

4. Plant Transformation

Per transformation 15 small leaves of a tobacco sterile culture which were wounded with sanding paper and a scalpel were placed in 10 ml MS medium containing 2% sucrose which contained 100 µl of a strictly selectively grown, transformed overnight culture of *Agrobacterium tumefaciens*.

After gently shaking the mixture for 15 minutes the leaves were placed on MS medium containing 1.6% glucose, 2 mg/l zeatin ribose, 0.02 mg/l naphthyl acetic acid, 0.02 mg giberellic acid, 500 mg/l Betabactyl®, 15 mg/l hygromycin and 0.8% Bacto agar. After incubation at 25° C. and 3,000 lux light intensity for one week, the Betabactyl concentration in the medium was reduced by half.

The examples illustrate the invention.

EXAMPLE 1

Isolation of Peptide Fragments of the 2-oxoglutarate/malate Translocator and Preparation of Probes for the Hybridization Screening of cDNA Libraries Purified 2-oxoglutarate/malate translocator protein (Menzlaff and Flügge, 1993, Biochim. Biophys. Acta 1147:13–18) was separated from remaining impurities in preparative SDS polyacrylamide gels (Laemmli, 1970, Nature 227:680–685) and cut out from the gel after detection of the protein by copper(II) sulfate staining (Lee et al., 1987, Anal. Biochem. 166:308–312) and digested in the gel matrix with endoproteinase LysC (Eckerskorn and Lottspeich, 1989, Chromatographia 28:92–94). The resulting peptides were eluted from the gel and separated via HPLC. The amino acid sequence of the purified peptide fractions was determined in the gaseous phase by automated Edman degradation (Eckerskorn et al., 1988, Eur. J. Biochem. 176:509–519). Degenerate oligonucleotide sequences coding for these amino acids were derived from the amino acid of three peptides and the respective oligonucleotides were prepared by in vitro DNA synthesis. For use as probe the oligonucleotides were radioactively labelled by affixing a $^{32}$p phosphate group to the 5' end via an oligonucleotide kinase.

EXAMPLE 2

Cloning of the 2-oxoglutarate/malate Translocator from Spinach

From young leaves of spinach plants grown in hydroculture poly-A+ RNA was isolated and on this basis a cDNA library was constructed in vector lambda gt10 (Flügge et al., 1989, EMBO J. 8:39–46). About 300,000 clones of this library were screened with synthetic oligonucleotides which were modelled after endoproteinase LysC peptide fragments of the purified 2-oxoglutarate/malate translocator (see Example 1). Positively reacting clones were purified by standard techniques and after preparation of the amplified phage DNA from the purified plaques the insert coding for the 2-oxoglutarate/malate translocator was obtained by EcoRI restriction digestion and verified by Southern blot analyses using the above-mentioned oligonucleotides as probe. After recloning of the inserts of the phage DNA into the vector pBluescript (pBSC) the clones were analyzed by determining the DNA sequence (didesoxy method: Sanger et al., 1977, Proc. Natl. Acad. Sci. USA 74:5463–5467) and from this DNA sequence the primary structure of the 2-oxoglutarate/malate translocator was derived. The sequence of the oligonucleotides or peptides used for screening the cDNA library could be recovered.

EXAMPLE 3

Expression of the 2-oxoglutarate/malate Translocator from Spinach in the Fission Yeast *Schizosaccharomyces Pombe*

The above-mentioned plasmid pBluescript (pBSC) containing the insert coding for the 2-oxoglutarate/malate translocator was linearized with the endonuclease SalI and the resulting cohesive ends were filled in with the enzyme T4-DNA polymerase. Then the insert was cut out from the vector by another restriction digestion with BamHI and isolated by electrophoresis. The fragment obtained in this manner was inserted in a specific orientation into the yeast expression vector pEVP11, which was first linearized with SacI, the ends filled up with T4-DNA polymerase and then digested again with BamHI (see also FIG. 2A) and, after amplification of the construct in *E. coli*, transformed in leucine synthesis deficient *S. pombe* cells which had been made competent by LiCl/PEG (Ito et al., 1983, J. Bact. 153:163–168). Transformants were selected without leucine by selection on minimum essential medium, since the pEVP11-211 construct imparts to the yeast cells the capability for growth on leucine-free medium.

EXAMPLE 4

Measurement of the Malate Transport Activity in Recombinant Yeast Lines

Yeast cells transformed with pEVP11-211 plasmid (see FIG. 2A, SP-DC3 cells) were grown in minimum essential medium up to an optical density of 1.0 at 600 nm and harvested by centrifugation at 3,000×g for 5 minutes. The cells were disrupted by vigorously shaking the mixture with ½ vol. (based on the cells) glass beads and glass beads and cell debris were separated by centrifugation (600 g for 1 minute). The supernatant was adjusted to a concentration of 0.5% (weight/volume) Triton X-100, an equal volume of liposomes was added to the mixture and the resulting proteoliposomes were immediately frozen in liquid nitrogen. The liposomes were previously prepared by sonification of soy bean phospholipid (20 mg/ml for 10 minutes at 4° C. in the presence of 200 mM tricine NaOH (pH 7.6), 40 mM malate and 60 mM potassium gluconate. After thawing of the proteoliposomes and sonification of the suspension with 10 pulses à 1 s the proteoliposomes were separated from the surrounding medium by size exclusion chromatography on Sephadex G-25 which had been equilibrated with 10 mM tricine NaOH (pH 7.6), 100 mM sodium gluconate and 50 mM potassium gluconate. The eluted proteoliposomes were used for measuring malate transport activity. The measurement was carried out according to the "inhibitor stop" method described by Menzlaff and Flügge (1993, Biochim. Biophys. Acta 1147:13–18).

Figure 1:
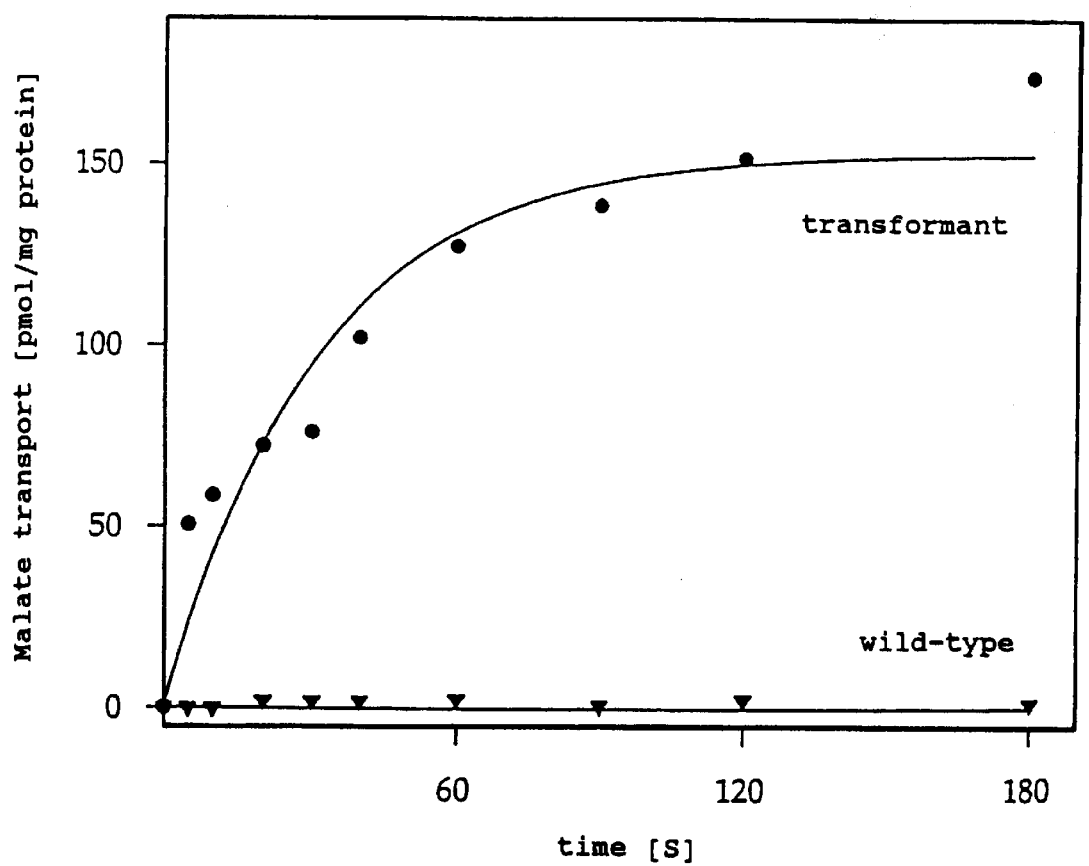
FIG. 1: Reconstitution of the transport activity of the recombinant 2-oxoglutarate/malate translocator expressed in yeast.

The malate transport activity in the 11-211 transformants was compared with the malate transport activity of transformants that were merely transformed with the vector pEVP11 without the 211 insert. It was found that the malate transport activity in the 11-211 transformants (measured in pmol of transported $^{14}C$ malate/mg protein *-hour) was 100-fold higher than in the pEVP11 control transformants. (FIG. 1). It furthermore could be demonstrated that the recombinant translocator protein exhibits identical transport characteristics as compared with the authentic protein of the chloroplast membrane. This finding is shown in the following table.

TABLE 1

Substrate specificity of the reconstituted 2-oxoglutarate/malate translocator

| Liposomes loaded with | Recombinant protein (transformed SP-DC3 cells) | Envelope membrane of spinach chloroplasts | Purified translocator protein* |
|---|---|---|---|
| Malate | (100) | (100) | (100) |
| Fumarate | 119 (±24) | 72 (±2) | 65 |
| Succinate | 83 (±12) | 74 (±2) | 63 |
| Glutarate | 63 (±14) | 52 (±1) | nd |
| 2-Oxoglutarate | 44 (±14) | 46 (±2) | 41 |
| Aspartate | 13 (±4) | 12 (±1) | 24 |
| Glutamate | 3 (±1) | 6 (±1) | 10 |
| Without substrate | 1 (±0) | 1 (±1) | 1 |

Whole yeast protein, envelope membrane proteins and the purified 2-oxoglutarate/malate translocator were reconstituted in liposomes which were preloaded with the indicated dicarboxylates. The transport activities were measured as described by Menzlaff and Flügge (Biochim. Biophys. Acta, 1993, 1147:13–18) and are indicated in the percentage of activity measured with malate-preloaded liposomes. The standard deviations are indicated in brackets. The 100% transport activities (nMol/mg protein per minute) were 0.8 (recombinant protein), 21.4 (envelope membranes) and 263 (purified translocator protein).
*Data by Menzlaff and Flügge (Biochim. Biophys. Acta, 1993, 1147:13–18)

EXAMPLE 5

Transformation of Plants with a Construct for the Over-expression of the Coding Region of the 2-oxoglutarate/malate Translocator From vector pBluescript-211 (pBSC-211) which contained as insert the cDNA for the 2-oxoglutarate/malate translocator from spinach (see Example 2, FIG. 2B) the insert was isolated by restriction digestion with EcoRV and SmaI and cloned into vector pBinAR (Höfgen and Willmitzer, 1990, Plant Sci.-66:221–230) which was digested with the enzyme SmaI. After amplification of the resulting construct pBinAR211 in *E. coli* the construct was transformed in agrobacteria and the latter were used to infect leave segments of tobacco and potato.

The resulting transformants were screened in Southern blot analyses for the presence of the intact, not rearranged chimeric gene. Using the "whole leave reconstitution method" (Flügge et Weber, 1994, Planta, 194:181–185) the malate transport activity was examined as compared to that of control transformants (transformed with vector pBinAR without insert), as well as the C/N ratio, photosynthesis rate, transpiration and growth.

EXAMPLE 6

Targeting of the 2-oxoglutarate/malate Translocator Precursor Protein to the Chloroplasts and Energy-dependent Insertion of the Mature Protein into the Inner Envelope Membrane The in vitro transcription of plasmid pBSC-211 which was linearized with SmaI was carried out using T3 RNA polymerase according to the instructions of the manufacturer (Pharmacia). Subsequent in vitro translation was carried out in the reticulocyte lysate (Boehringer-Mannheim). The post-ribosomal supernatant was used for protein transports in intact spinach chloroplasts. The experiment was carried out in the dark as well as in the light; the preparation contained import buffer (Flügge et al., 1989, EMBO J. 8:39–46), intact spinach chloroplasts (corresponding to 200 mg chlorophyll) and various additives indicated in the legend to FIG. 3 (entire volume: 300 ml). After 15 minutes at 25° C. the chloroplasts were washed and the envelope membranes were isolated (Flügge et al., 1989, EMBO J. 8:39–46) were isolated. They were analyzed in a SDS polyacrylamide gel electrophoresis (Laemmli, 1970, Nature 227:680–685) and subsequent fluorography (Bonner and Laskey, 1974, Eur. J. Biochem. 46:84–88) (FIG. 3). Lane 1 shows the in vitro translated precursor protein (p). Lanes 2–4: dark conditions, lanes 5–9: light conditions. Under all conditions the presequence of the 2-oxoglutarate/malate translocator directs the affixed mature protein correctly to its target membrane, the inner envelope membrane of the chloroplasts; it is cleaved during the import process by a specific protease; the mature protein (m) is formed. In the dark the insertion of the translocator is provided with energy by adding ATP (lanes 3 and 4). In the absence of ATP (lane 1) no import is observed. In the light the energy for the import of the protein can be provided in the form of ATP via photosynthetic phosphorylation; the import under these conditions is independent of exogenous ATP (lane 5) but can be increased by ATP added from the exterior (lane 6). If photosynthetic phosphorylation and the resulting production of ATP is prevented by adding a decoupling agent such as CCCP, the protein import is blocked (lane 8). The mature protein is present incorporated in the inner membrane: addition of proteases (e.g., thermolysine), which cannot permeate the outer envelope membrane are not capable of affecting the mature protein incorporated in the inner membrane (lanes 4 and 7). A pretreatment of the chloroplasts with a protease (e.g., thermolysine) leads to the complete loss of the binding and of the import of the translocator (lane 9). This goes to show that the presequence (targeting sequence) of the translocator in a first step needs to be specifically bound to receptors located on the outer membrane. Only then the further steps of protein-insertion can be taken.

What is claimed is:

1. A transgenic plant cell comprising a DNA molecule introduced into said plant cell, wherein said DNA molecule is selected from the group consisting of:
   (a) a DNA molecule coding for a protein comprising the amino acid sequence of SEQ ID NO:2;
   (b) a DNA molecule comprising the nucleotide sequence of SEQ ID NO:1;
   (c) a DNA molecule that hybridizes under low stringency conditions to the DNA molecule of (a) or (b), wherein the hybridizing DNA molecule encodes a protein having plastid 2-oxoglutarate/malate translocator activity;
   (d) a DNA molecule the sequence of which is degenerate as a result of the genetic code compared to the sequence of the DNA molecule of (a), (b) or (c);
   (e) a DNA molecule that is complementary to the sequence of the DNA molecule of (a), (b), (c) or (d); and
   (f) a recombinant DNA molecule comprising the DNA molecule according to any one of the DNA molecules of (a), (b), (c), (d) or (e).

2. A transgenic plant regenerated from the plant cell according to claim 1, or comprising the plant cell according to claim 1.

3. A transgenic plant cell comprising plasmid pBinAR-211, deposited as DSM 9239 in E. coli strain TG1 pBinAR-211.

4. A transgenic plant regenerated from a plant cell, wherein said plant cell comprises a recombinant DNA molecule introduced into said plant cell, and wherein said recombinant DNA molecule comprises a DNA molecule selected from the group consisting of:
   (a) a DNA molecule coding for a protein comprising the amino acid sequence of SEQ ID NO:2;
   (b) a DNA molecule comprising the nucleotide sequence of SEQ ID NO:1;
   (c) a DNA molecule that hybridizes under low stringency conditions to the DNA molecule of (a) or (b), wherein the hybridizing DNA molecule encodes a protein having plastid 2-oxoglutarate/malate translocator activity;
   (d) a DNA molecule the sequence of which is degenerate as a result of the genetic code compared to the sequence of the DNA molecule of (a), (b) or (c); and
   (e) a DNA molecule that is complementary to the sequence of the DNA molecule of (a), (b), (c) or (d).

5. A transgenic plant comprising a plant cell, wherein a recombinant DNA molecule is introduced into said plant cell, and wherein said recombinant DNA molecule comprises a DNA molecule selected from the group consisting of:
   (a) a DNA molecule coding for a protein comprising the amino acid sequence of SEQ ID NO:2;
   (b) a DNA molecule comprising the nucleotide sequence of SEQ ID NO:1;
   (c) a DNA molecule that hybridizes under low stringency conditions to the DNA molecule of (a) or (b), wherein the hybridizing DNA molecule encodes a protein having plastid 2-oxoglutarate/malate translocator activity;
   (d) a DNA molecule the sequence of which is degenerate as a result of the genetic code compared to the sequence of the DNA molecule of (a), (b) or (c); and
   (e) a DNA molecule that is complementary to the sequence of the DNA molecule of (a), (b), (c) or (d).

6. The transgenic plant cell according to claim 1, wherein said DNA molecule codes for a protein comprising the amino acid sequence of SEQ ID NO:2.

7. A transgenic plant regenerated from the plant cell according to claim 6 or comprising the plant cell according to claim 6.

8. The transgenic plant cell according to claim 6, wherein the DNA molecule comprises the nucleoride sequence of SEQ ID NO:1.

9. A transgenic plant regenerated from the plant cell according to claim 8 or comprising the plant cell according to claim 8.

10. A transgenic plant regenerated from the plant cell according to claim 3 or comprising the plant cell according to claim 3.

11. The transgenic plant according to claim 4, wherein said DNA molecule codes for a protein comprising the amino acid sequence of SEQ ID NO:2.

12. The transgenic plant according to claim 11, wherein said DNA molecule comprises the nucleotide sequence of SEQ ID NO:1.

13. The transgenic plant according to claim 5, wherein said DNA molecule codes for a protein comprising the amino acid sequence of SEQ ID NO:2.

14. The transgenic plant according to claim 13, wherein said DNA molecule comprises the nucleotide sequence of SEQ ID NO.1.

15. A seed from the transgenic plant according to claim 2, wherein the seed comprises said DNA molecule.

16. A seed from the transgenic plant according to claim 10, wherein the seed comprises said DNA molecule.

17. A seed from the transgenic plant according to claim 4, wherein the seed comprises said recombinant DNA molecule.

18. A seed from the transgenic plant according to claim 5, wherein the seed comprises said recombinant DNA molecule.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1945 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Spinacia oleracea (vii) IMMEDIATE SOURCE:
      (A) LIBRARY: cDNA library in phage lambda gt10

(ix) FEATURE:
      (A) NAME/KEY: CDS
      (B) LOCATION:14..1720
      (D) OTHER INFORMATION:/note=
        "2-Oxoglutarate/malate-translocator"

(xi) SEQUENCE DESCRIPTION: SEQ ID NO: 1:

```
GGAGCCTTCA ACA ATG GCG TCC ATG GCT CTG AGT CTA ACT TCA TCT CCT           49
            Met Ala Ser Met Ala Leu Ser Leu Thr Ser Ser Pro
              1               5                  10

ACC TAC TCT CTC TCC TTC AGA TCT CTC CCT TCT CTC AAA CCT CTC TCC          97
Thr Tyr Ser Leu Ser Phe Arg Ser Leu Pro Ser Leu Lys Pro Leu Ser
         15                  20                  25

AAA TCT CAA CCC TCC ATT TCC CTC CCT TCT CTC AGA TCC AAC GCT TCA         145
Lys Ser Gln Pro Ser Ile Ser Leu Pro Ser Leu Arg Ser Asn Ala Ser
     30                  35                  40

AAA TCT CCA TCT CTC TCA CAC AAA CAC TTC CTC TCT CCT CCT TCT CTT         193
Lys Ser Pro Ser Leu Ser His Lys His Phe Leu Ser Pro Pro Ser Leu
 45                  50                  55                  60

CTC CTC CCT CAC AAA CTC AAA CCC ATT TCA GCT TCT TCC CCA ACA AAC         241
Leu Leu Pro His Lys Leu Lys Pro Ile Ser Ala Ser Ser Pro Thr Asn
```

-continued

| | | | | | | | | | | | | | | | |
|---|---|---|---|---|---|---|---|---|---|---|---|---|---|---|---|
| | | | | 65 | | | | | 70 | | | | | 75 | |
| CCA | CCT | CCA | CCT | CCA | GCT | CCA | GTC | CCC | TCC | CCA | GCT | CCA | GTT | TCA | GCT | 289
| Pro | Pro | Pro | Pro | Pro | Ala | Pro | Val | Pro | Ser | Pro | Ala | Pro | Val | Ser | Ala |
| | | | 80 | | | | | 85 | | | | | 90 | | |

| CCA | GCT | CAA | GTT | CAG | CCA | TGG | CAG | GGA | GCT | TCA | ATC | AAA | CCT | CTA | CTC | 337
| Pro | Ala | Gln | Val | Gln | Pro | Trp | Gln | Gly | Ala | Ser | Ile | Lys | Pro | Leu | Leu |
| | | 95 | | | | | 100 | | | | | 105 | | | |

| GCA | TCA | ATC | TTA | ACA | GGT | GTC | ATA | ATC | TGG | TTC | ATC | CCT | ACA | CCA | GAG | 385
| Ala | Ser | Ile | Leu | Thr | Gly | Val | Ile | Ile | Trp | Phe | Ile | Pro | Thr | Pro | Glu |
| | 110 | | | | | 115 | | | | | 120 | | | | |

| GGA | GTC | TCC | AGA | AAC | GCA | TGG | CAA | CTC | CTC | GCA | ATC | TTC | CTC | TCC | ACC | 433
| Gly | Val | Ser | Arg | Asn | Ala | Trp | Gln | Leu | Leu | Ala | Ile | Phe | Leu | Ser | Thr |
| 125 | | | | | 130 | | | | | 135 | | | | | 140 |

| ATT | GTT | GGA | ATC | ATC | ACT | CAA | CCT | TTA | CCT | TTG | GGT | GCC | GTT | GCA | TTG | 481
| Ile | Val | Gly | Ile | Ile | Thr | Gln | Pro | Leu | Pro | Leu | Gly | Ala | Val | Ala | Leu |
| | | | | 145 | | | | | 150 | | | | | 155 | |

| ATG | GGG | TTA | GGC | GCT | TCA | GTT | TTG | ACA | AAA | ACC | CTA | ACA | TTC | TCC | GCC | 529
| Met | Gly | Leu | Gly | Ala | Ser | Val | Leu | Thr | Lys | Thr | Leu | Thr | Phe | Ser | Ala |
| | | | 160 | | | | | 165 | | | | | 170 | | |

| GCG | TTT | TCC | GCT | TTC | GGT | GAC | CCA | ATT | CCA | TGG | TTG | ATC | GCT | CTC | GCC | 577
| Ala | Phe | Ser | Ala | Phe | Gly | Asp | Pro | Ile | Pro | Trp | Leu | Ile | Ala | Leu | Ala |
| | | 175 | | | | | 180 | | | | | 185 | | | |

| TTC | TTC | TTC | GCT | CGT | GGG | TTC | ATC | AAA | ACT | GGA | CTC | GGG | AAT | CGA | ATT | 625
| Phe | Phe | Phe | Ala | Arg | Gly | Phe | Ile | Lys | Thr | Gly | Leu | Gly | Asn | Arg | Ile |
| | 190 | | | | | 195 | | | | | 200 | | | | |

| GCG | TAC | CAA | TTT | GTG | AAA | CTA | TTT | GGG | AGT | TCT | TCA | TTA | GGG | TTA | GGT | 673
| Ala | Tyr | Gln | Phe | Val | Lys | Leu | Phe | Gly | Ser | Ser | Ser | Leu | Gly | Leu | Gly |
| 205 | | | | | 210 | | | | | 215 | | | | | 220 |

| TAC | AGT | CTT | GTT | TTC | AGT | GAA | GCC | CTT | TTA | GCC | CCT | GCA | ATT | CCT | TCT | 721
| Tyr | Ser | Leu | Val | Phe | Ser | Glu | Ala | Leu | Leu | Ala | Pro | Ala | Ile | Pro | Ser |
| | | | | 225 | | | | | 230 | | | | | 235 | |

| GTT | TCT | GCA | AGA | GCA | GGT | GGG | ATT | TTC | CTT | CCA | TTG | GTG | AAA | TCC | CTG | 769
| Val | Ser | Ala | Arg | Ala | Gly | Gly | Ile | Phe | Leu | Pro | Leu | Val | Lys | Ser | Leu |
| | | | 240 | | | | | 245 | | | | | 250 | | |

| TGT | ATT | GCT | TGT | GGT | AGC | AAT | GTG | GGT | GAT | GGA | ACT | GAG | AGG | AAA | TTG | 817
| Cys | Ile | Ala | Cys | Gly | Ser | Asn | Val | Gly | Asp | Gly | Thr | Glu | Arg | Lys | Leu |
| | | 255 | | | | | 260 | | | | | 265 | | | |

| GGG | GCT | TGG | TTG | ATG | CTT | ACA | TGT | TTC | CAA | ACT | TCT | GTG | ATT | TCT | AGC | 865
| Gly | Ala | Trp | Leu | Met | Leu | Thr | Cys | Phe | Gln | Thr | Ser | Val | Ile | Ser | Ser |
| | 270 | | | | | 275 | | | | | 280 | | | | |

| TCT | ATG | TTT | TTA | ACT | GCT | ATG | GCT | GCT | AAT | CCT | TTG | AGT | GCA | ACT | TTG | 913
| Ser | Met | Phe | Leu | Thr | Ala | Met | Ala | Ala | Asn | Pro | Leu | Ser | Ala | Thr | Leu |
| 285 | | | | | 290 | | | | | 295 | | | | | 300 |

| ACA | TTC | AAT | ACT | ATT | GGT | AAG | GCA | ATT | GGG | TGG | ATG | GAT | TGG | GCT | AAA | 961
| Thr | Phe | Asn | Thr | Ile | Gly | Lys | Ala | Ile | Gly | Trp | Met | Asp | Trp | Ala | Lys |
| | | | | 305 | | | | | 310 | | | | | 315 | |

| GCT | GCT | TTT | GTT | CCT | GGG | TTG | GTT | TCT | TTG | ATT | GTT | GTT | CCT | TTA | CTG | 1009
| Ala | Ala | Phe | Val | Pro | Gly | Leu | Val | Ser | Leu | Ile | Val | Val | Pro | Leu | Leu |
| | | | 320 | | | | | 325 | | | | | 330 | | |

| TTG | TAT | GTG | GTT | TAC | CCT | CCT | GAG | ATT | AAG | TCT | AGT | CCT | GAT | GCT | CCT | 1057
| Leu | Tyr | Val | Val | Tyr | Pro | Pro | Glu | Ile | Lys | Ser | Ser | Pro | Asp | Ala | Pro |
| | | 335 | | | | | 340 | | | | | 345 | | | |

| CGC | CTT | GCC | AAA | GAG | AAG | TTG | GAC | AAG | ATG | GGT | CCT | ATG | ACA | AAG | AAT | 1105
| Arg | Leu | Ala | Lys | Glu | Lys | Leu | Asp | Lys | Met | Gly | Pro | Met | Thr | Lys | Asn |
| | 350 | | | | | 355 | | | | | 360 | | | | |

| GAG | AGC | ATT | ATG | GCT | GTC | ACT | TTG | CTT | CTC | ACG | GTG | GGA | TTG | TGG | GTT | 1153
| Glu | Ser | Ile | Met | Ala | Val | Thr | Leu | Leu | Leu | Thr | Val | Gly | Leu | Trp | Val |
| 365 | | | | | 370 | | | | | 375 | | | | | 380 |

| TTC | GGA | GGA | AAG | TTG | GGC | GTT | GAT | GCA | GTC | ACT | GCG | GCA | ATT | CTT | GGA | 1201

```
Phe Gly Gly Lys Leu Gly Val Asp Ala Val Thr Ala Ala Ile Leu Gly
                385                 390                 395

TTA TCC GTG CTC CTC ATA ACT GGT GTT GTC ACC TGG AAA GAG TGC TTA       1249
Leu Ser Val Leu Leu Ile Thr Gly Val Val Thr Trp Lys Glu Cys Leu
            400                 405                 410

GCC GAG TCA GTT GCA TGG GAT ACC CTC ACA TGG TTT GCT GCA CTC ATT       1297
Ala Glu Ser Val Ala Trp Asp Thr Leu Thr Trp Phe Ala Ala Leu Ile
        415                 420                 425

GCC ATG GCT GGT TAT CTC AAC AAG TAC GGT CTC ATT ACC TGG TTC AGT       1345
Ala Met Ala Gly Tyr Leu Asn Lys Tyr Gly Leu Ile Thr Trp Phe Ser
    430                 435                 440

GAA AAT GTG GTT AAG GTT GTT GGT GGT TTA GGT CTT TCA TGG CAG ATG       1393
Glu Asn Val Val Lys Val Val Gly Gly Leu Gly Leu Ser Trp Gln Met
445                 450                 455                 460

TCA TTC GGC GTT CTA GTT CTT CTT TAC TTC TAC TCT CAC TAC TTC TTT       1441
Ser Phe Gly Val Leu Val Leu Leu Tyr Phe Tyr Ser His Tyr Phe Phe
                465                 470                 475

GCT AGT GGA GCT GCA CAT ATT GGT GCC ATG TTC ACA GCC TTC CTT TCA       1489
Ala Ser Gly Ala Ala His Ile Gly Ala Met Phe Thr Ala Phe Leu Ser
            480                 485                 490

GTT GCA AGT GCA CTA GGG ACT CCA CCA TTC TTG GCA GCC ATT GTT CTT       1537
Val Ala Ser Ala Leu Gly Thr Pro Pro Phe Leu Ala Ala Ile Val Leu
        495                 500                 505

TCA TTC CTC TCC AAT CTT ATG GGT GGA CTC ACC CAC TAC GGT ATT GGT       1585
Ser Phe Leu Ser Asn Leu Met Gly Gly Leu Thr His Tyr Gly Ile Gly
    510                 515                 520

TCA GCC CCC GTT TTC TAC GGT GCT AAC TAT GTT CCC CTA CCA CAA TGG       1633
Ser Ala Pro Val Phe Tyr Gly Ala Asn Tyr Val Pro Leu Pro Gln Trp
525                 530                 535                 540

TGG GGT TAC GGT TTC CTC ATC TCA ATA GTT AAC TTG ATA ATC TGG CTC       1681
Trp Gly Tyr Gly Phe Leu Ile Ser Ile Val Asn Leu Ile Ile Trp Leu
                545                 550                 555

GGA GTT GGG GGA CTT TGG TGG AAA GCT ATT GGA TTG TGG TGATCAGGTT        1730
Gly Val Gly Gly Leu Trp Trp Lys Ala Ile Gly Leu Trp
            560                 565

GGTGCTCGTT CGTAGAATTT GTTGACCCTG CAATTTAGTA CTTCTCGCGA ATACTTGCCT    1790

ATTATATACA AGCTCTTCCT AGAGGTAGCC CTCTGCATTT TTGTTTTTGA TTCTTTGTTT    1850

CTTAGAAAAT TTAATCCCCC TTTGTCTCTG CGAAATGAAA CAGATCATGA AATATAAAGA    1910

GCAAATAGT TCAAATTTGT TTTAAAAAAA AAAA                                 1945

(2) INFORMATION FOR SEQ ID NO: 2:

(i) SEQUENCE CHARACTERISTICS:
        (A) LENGTH: 569 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ser Met Ala Leu Ser Leu Thr Ser Ser Pro Thr Tyr Ser Leu
  1               5                  10                  15

Ser Phe Arg Ser Leu Pro Ser Leu Lys Pro Leu Ser Lys Ser Gln Pro
             20                  25                  30

Ser Ile Ser Leu Pro Ser Leu Arg Ser Asn Ala Ser Lys Ser Pro Ser
         35                  40                  45

Leu Ser His Lys His Phe Leu Ser Pro Pro Ser Leu Leu Leu Pro His
     50                  55                  60
```

-continued

```
Lys Leu Lys Pro Ile Ser Ala Ser Ser Pro Thr Asn Pro Pro Pro
 65                  70                  75                  80

Pro Ala Pro Val Pro Ser Pro Ala Pro Val Ser Ala Pro Ala Gln Val
                 85                  90                  95

Gln Pro Trp Gln Gly Ala Ser Ile Lys Pro Leu Leu Ala Ser Ile Leu
            100                 105                 110

Thr Gly Val Ile Ile Trp Phe Ile Pro Thr Pro Glu Gly Val Ser Arg
            115                 120                 125

Asn Ala Trp Gln Leu Leu Ala Ile Phe Leu Ser Thr Ile Val Gly Ile
        130                 135                 140

Ile Thr Gln Pro Leu Pro Leu Gly Ala Val Ala Leu Met Gly Leu Gly
145                 150                 155                 160

Ala Ser Val Leu Thr Lys Thr Leu Thr Phe Ser Ala Ala Phe Ser Ala
                165                 170                 175

Phe Gly Asp Pro Ile Pro Trp Leu Ile Ala Leu Ala Phe Phe Phe Ala
            180                 185                 190

Arg Gly Phe Ile Lys Thr Gly Leu Gly Asn Arg Ile Ala Tyr Gln Phe
        195                 200                 205

Val Lys Leu Phe Gly Ser Ser Ser Leu Gly Leu Gly Tyr Ser Leu Val
    210                 215                 220

Phe Ser Glu Ala Leu Leu Ala Pro Ala Ile Pro Ser Val Ser Ala Arg
225                 230                 235                 240

Ala Gly Gly Ile Phe Leu Pro Leu Val Lys Ser Leu Cys Ile Ala Cys
                245                 250                 255

Gly Ser Asn Val Gly Asp Gly Thr Glu Arg Lys Leu Gly Ala Trp Leu
            260                 265                 270

Met Leu Thr Cys Phe Gln Thr Ser Val Ile Ser Ser Met Phe Leu
        275                 280                 285

Thr Ala Met Ala Ala Asn Pro Leu Ser Ala Thr Leu Thr Phe Asn Thr
        290                 295                 300

Ile Gly Lys Ala Ile Gly Trp Met Asp Trp Ala Lys Ala Ala Phe Val
305                 310                 315                 320

Pro Gly Leu Val Ser Leu Ile Val Val Pro Leu Leu Leu Tyr Val Val
                325                 330                 335

Tyr Pro Pro Glu Ile Lys Ser Ser Pro Asp Ala Pro Arg Leu Ala Lys
            340                 345                 350

Glu Lys Leu Asp Lys Met Gly Pro Met Thr Lys Asn Glu Ser Ile Met
        355                 360                 365

Ala Val Thr Leu Leu Leu Thr Val Gly Leu Trp Val Phe Gly Gly Lys
    370                 375                 380

Leu Gly Val Asp Ala Val Thr Ala Ala Ile Leu Gly Leu Ser Val Leu
385                 390                 395                 400

Leu Ile Thr Gly Val Val Thr Trp Lys Glu Cys Leu Ala Glu Ser Val
                405                 410                 415

Ala Trp Asp Thr Leu Thr Trp Phe Ala Ala Leu Ile Ala Met Ala Gly
            420                 425                 430

Tyr Leu Asn Lys Tyr Gly Leu Ile Thr Trp Phe Ser Glu Asn Val Val
        435                 440                 445

Lys Val Val Gly Gly Leu Gly Leu Ser Trp Gln Met Ser Phe Gly Val
    450                 455                 460

Leu Val Leu Leu Tyr Phe Tyr Ser His Tyr Phe Ala Ser Gly Ala
465                 470                 475                 480
```

-continued

```
Ala His Ile Gly Ala Met Phe Thr Ala Phe Leu Ser Val Ala Ser Ala
                485             490             495

Leu Gly Thr Pro Pro Phe Leu Ala Ala Ile Val Leu Ser Phe Leu Ser
            500             505             510

Asn Leu Met Gly Gly Leu Thr His Tyr Gly Ile Gly Ser Ala Pro Val
        515             520             525

Phe Tyr Gly Ala Asn Tyr Val Pro Leu Pro Gln Trp Trp Gly Tyr Gly
    530             535             540

Phe Leu Ile Ser Ile Val Asn Leu Ile Ile Trp Leu Gly Val Gly Gly
545             550             555             560

Leu Trp Trp Lys Ala Ile Gly Leu Trp
                565
```